United States Patent
Lahrman et al.

(10) Patent No.: US 6,462,308 B1
(45) Date of Patent: Oct. 8, 2002

(54) UTILIZING ALTERED VIBRATION RESPONSES OF WORKPIECES, SUCH AS GAS TURBINE ENGINE BLADES

(75) Inventors: David F. Lahrman, Powell; Allan H. Clauer, Worthington, both of OH (US)

(73) Assignee: LSP Technologies, Inc., Dublin, OH (US)

(*) Notice: Subject to any disclaimer, the term of this patent is extended or adjusted under 35 U.S.C. 154(b) by 0 days.

(21) Appl. No.: 09/448,683

(22) Filed: Nov. 23, 1999

(51) Int. Cl.[7] .............................................. B23K 26/00
(52) U.S. Cl. .............................. 219/121.85; 219/121.83
(58) Field of Search ...................... 219/121.85, 121.62, 219/121.78, 121.79, 121.8, 121.82, 121.69, 121.83, 121.61

(56) References Cited

U.S. PATENT DOCUMENTS

| | | | | |
|---|---|---|---|---|
| 4,401,477 A | * | 8/1983 | Clauer et al. | 148/4 |
| 5,131,957 A | * | 7/1992 | Epstein et al. | 148/565 |
| 5,988,982 A | * | 11/1999 | Clauer | 416/241 R |

* cited by examiner

Primary Examiner—M. Alexandra Elve
(74) Attorney, Agent, or Firm—Randall J. Knuth (57) ABSTRACT

An apparatus and method of utilizing natural frequency shifts of a laser shock processed workpiece to determine if sufficient laser shock processing has been accomplished.

20 Claims, 9 Drawing Sheets

UTILIZING ALTERED VIBRATION RESPONSES OF WORKPIECES, SUCH AS GAS TURBINE ENGINE BLADES

CROSS-REFERENCE TO RELATED APPLICATIONS

This application is related to co-pending application entitled ALTERING VIBRATION FREQUENCIES OF WORKPIECES, SUCH AS GAS TURBINE ENGINE BLADES, U.S. patent application Ser. No. 08/962,622, now U.S. Pat. No. 5,988,982.

This invention was made with United States Government support under Contract No. F33615-98-C-5150 awarded by the Department of the Air Force. The United States Government has certain rights to this invention.

BACKGROUND OF THE INVENTION

1. Field of the Invention

The present invention relates to the use of coherent energy pulses, as from high powered pulse lasers, in shock processing of solid materials, and more particularly to methods and apparatus for determining if sufficient laser shock processing has occurred by determining vibrational frequency and mode shapes of workpieces, such as gas turbine engine blades.

2. Description of the Related Art.

Airfoil failures, i.e., cracking, separation, and distortion, result from a number of different causes, one being vibratory resonance. Gas turbine engine blades occasionally respond in their operating envelope by resonant mode vibration between their start, idle and maximum RPM speeds.

Laser shock processing has been used for processing metal parts as shown U.S. patent application Ser. No. 08/962,622, now U.S. Pat. No. 5,988,982, laser peening systems may change the vibrational frequencies of most workpieces, such as gas turbine engine blades.

SUMMARY OF THE INVENTION

According to the present invention a method for determining the vibration characteristics of a workpiece, particularly a gas turbine engine blade, is taught. Laser shock peening is applied to locations on the workpiece, particularly to areas of high bending strains between or near the nodal lines for a particular preselected vibration mode. The use of laser shock peening is used to modify the airfoil or the workpiece natural vibration frequencies and mode shapes to improve their operating characteristics.

The invention, in one form thereof, includes a method for determining that a production workpiece has been sufficiently laser shock peened, the method comprising the steps of: determining a natural frequency of a test workpiece before laser shock peening said test workpiece; determining the frequency shift of said natural frequency of said test workpiece after said test workpiece has been laser shock peened; comparing said frequency shift to a predetermined acceptable range of frequency shift for said test workpiece; processing production workpieces if said frequency.

The invention includes a method for determining that the laser shock peening processing conditions are within an acceptable range, the method comprising the steps of: determining a natural frequency of a test workpiece before laser shock peening said test workpiece; determining the frequency shift of said natural frequency of said test workpiece after said test workpiece has been laser shock peened; comparing said frequency shift to a predetermined acceptable range of frequency shift for said test workpiece; and processing production workpieces if said frequency shift is within said acceptable range of frequency shift.

In another form of the invention, a method is described for determining that a workpiece has been sufficiently laser shock processed, the method comprising the steps of: determining a natural frequency of a laser peened workpiece; and comparing said determined natural frequency to a predetermined natural frequency indicative of a sufficiently laser shock peened workpiece.

Another form of the invention includes an apparatus for determining that a workpiece has been sufficiently laser shock processed, the apparatus comprising:

a laser to laser shock process a workpiece;

a frequency measuring device to measure a natural frequency of the workpiece operatively associated with said laser;

comparing means for comparing said natural frequency to the acceptable condition of one of range of frequency and frequency shift for the workpiece, wherein if said frequency shift or frequency is not within the acceptable range, said means causes said laser to again laser shock process the workpiece until said natural frequency condition is satisfied.

An advantage of the present invention is that a natural frequency shift of the laser peened part may not be used to determine whether or not a sufficient laser peening activity has been accomplished on the part. Such a measurement of the frequency shift is a non-destructive evaluation technique suitable for a production processing environment of workpieces, such as gas turbine engine blades.

An advantage of the present invention is that it reduces vibratory amplitudes that may damage the workpiece, such as gas turbine engine blades, at particular frequencies. Such change in vibration frequency and mode shape may improve workpiece or blade lifetime, and for blades, the engine operating envelope.

Another advantage of the present invention is, the use of laser shock peening can be utilized to modify the airfoil and vibration frequencies and mode shapes in the design stage to improve the operating characteristics of the blade and engine. Additionally, the method may be used for an after-manufacturing solution to vibration problems encountered during engine operations or modification of existing blades to minimize a potential problem.

A further advantage of the invention is that by moving the resonance frequency of the workpiece by a fraction, even as small a range as two to five percent, high amplitude beating at a particular initial resonance frequency is eliminated, thereby reducing high fatigue stresses at the node of that vibration mode.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Laser shock peening has been used in the past as an effective method of increasing fatigue life in metal by treating fatigue critical regions. In the prior history of laser shock processing and that of high powered processing of engineered materials, reference can be made to U.S. Pat. No. 5,131,957. This patent shows a type of laser and laser circuit adaptable for use of the present invention. Another type of laser adaptable for use of the invention, is that with a Nd-glass laser manufactured by LSP Technologies of Dublin, Ohio.

In accordance with the present invention, the use of opaque classic overlays is known with standard laser shock processing of laser peening processing. Such descriptions of transparent and opaque laser peening overlays used with the process are not discussed here.

The present invention includes utilization of laser shock processing to shift the vibratory resonance condition of a workpiece, such as a gas turbine engine airfoil, and use such shift to verify sufficient laser peening power and activity as been applied to the workpiece.

Figure 1:
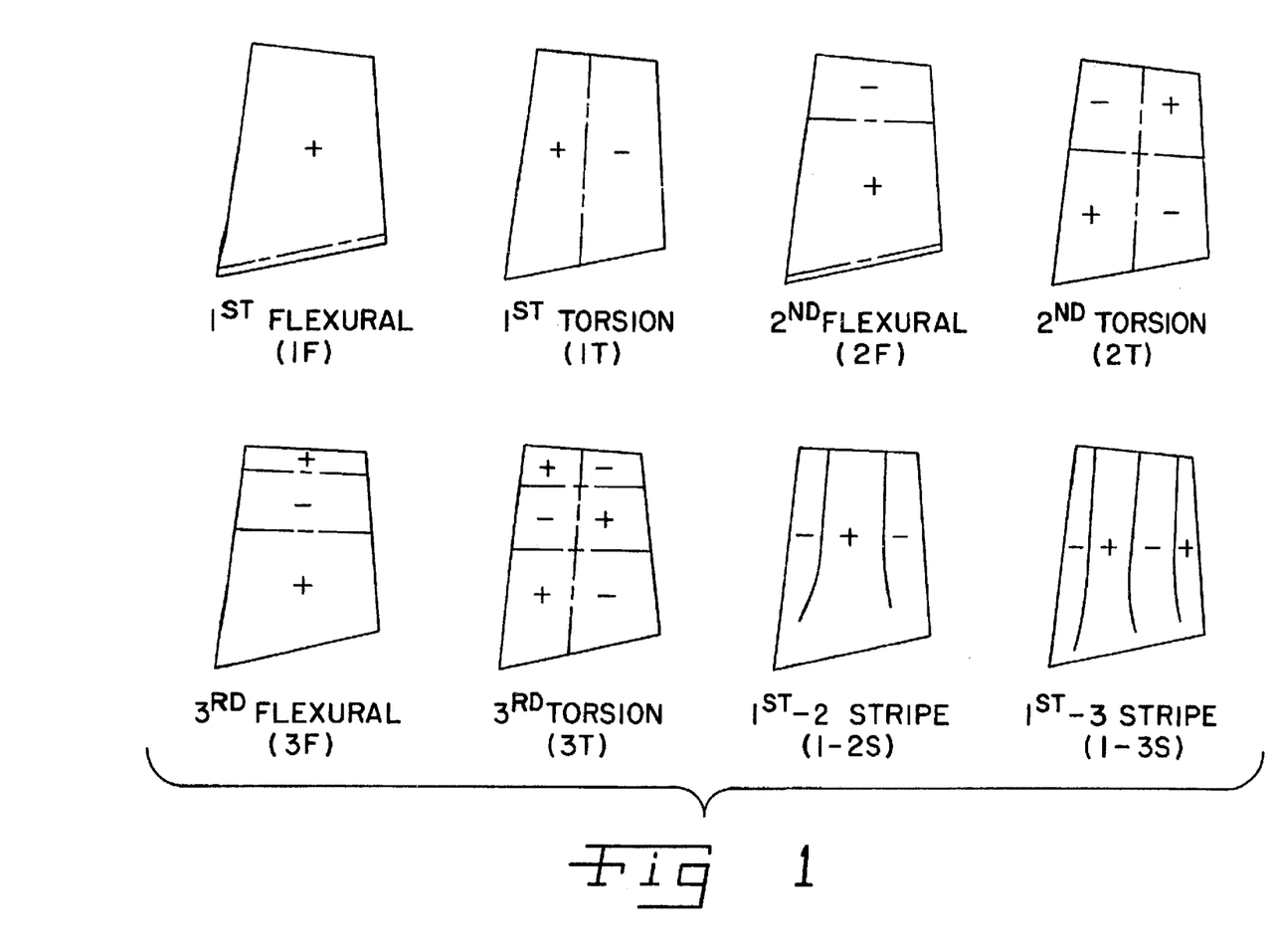
FIG. 1 is a collection of ideal resonance mode shapes for a workpiece, particularly a gas turbine engine airfoil.
Figure 2:
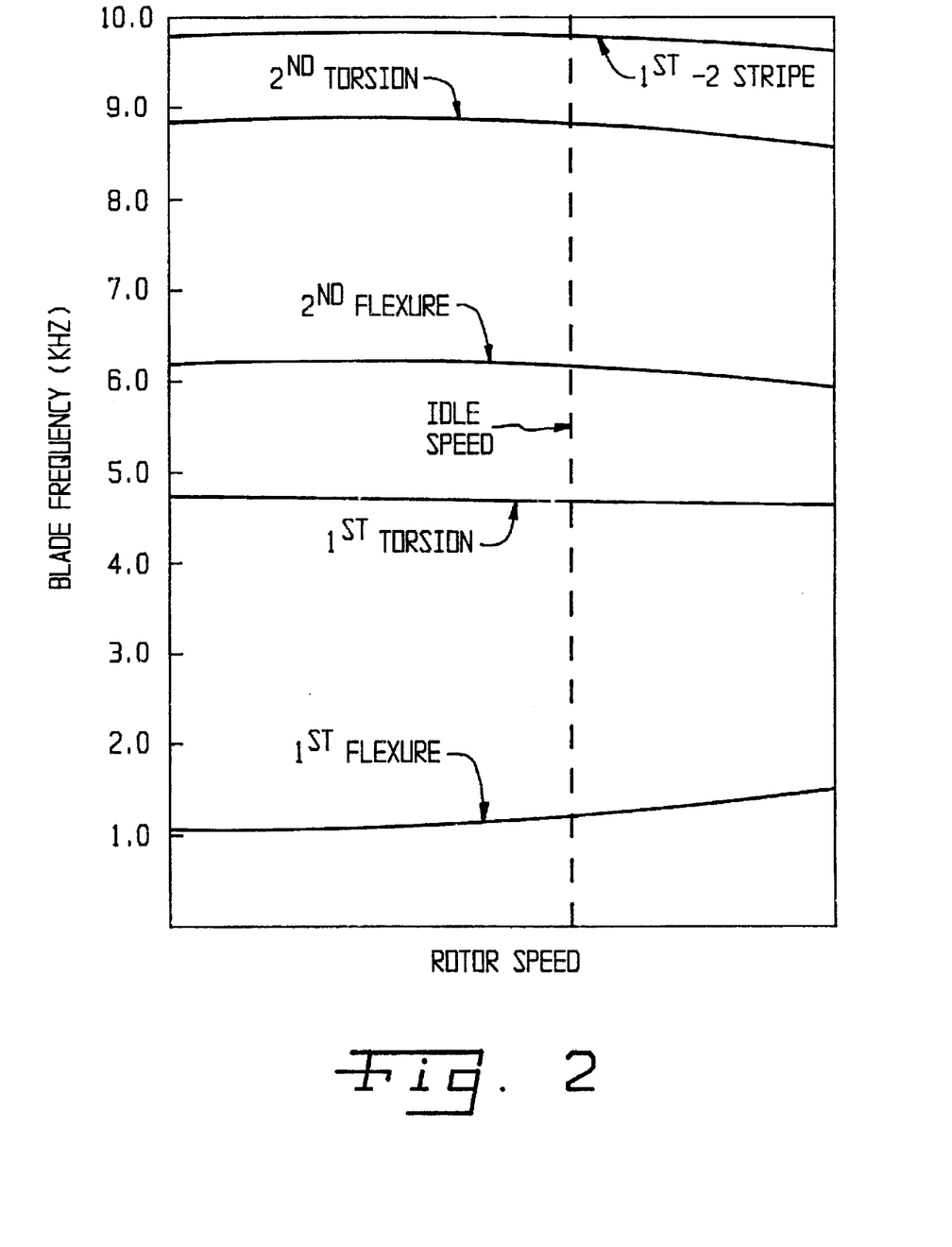
FIG. 2 is a representative graph showing blade resonance frequency compared to gas turbine engine rotor speed, showing particular example resonance modes.

FIG. 1, shows exemplary or ideal vibration modes for a workpiece, particularly a gas turbine engine airfoil. Such modes may be formed when the gas turbine engine, to which the airfoil attached, is operated at a particular rotor speeds, as shown in FIG. 2.

Laser shock peening is known to create deep residual compressive stress within the workpiece so peened. Prior to the invention, on investigation by the present inventor, no knowledge or teaching of affecting the natural vibrational frequency response in a workpiece has been shown by laser shock peening, or any other method of shock peening by creating residual compressive stresses.

Operating stresses or externally applied stresses affect the natural frequencies of beams, shells, and airfoils. The trend is for many natural frequencies to increase under a tensile stress and to decrease under a compressive stress. For example, the natural vibration frequencies of airfoils rotating in gas turbine engines increase with increasing RPM. However, there is no known teaching where the intrinsic stresses within the workpieces change the natural frequency. Laser shock peening is able to introduce high compressive residual stresses within a large enough volume of the workpiece to enable the natural frequencies to be modified in a controlled way over a significant range for practical use. These changes in the natural frequencies are independent of the operating stresses, and enable the airfoil or workpiece to be "tuned".

Figure 3:
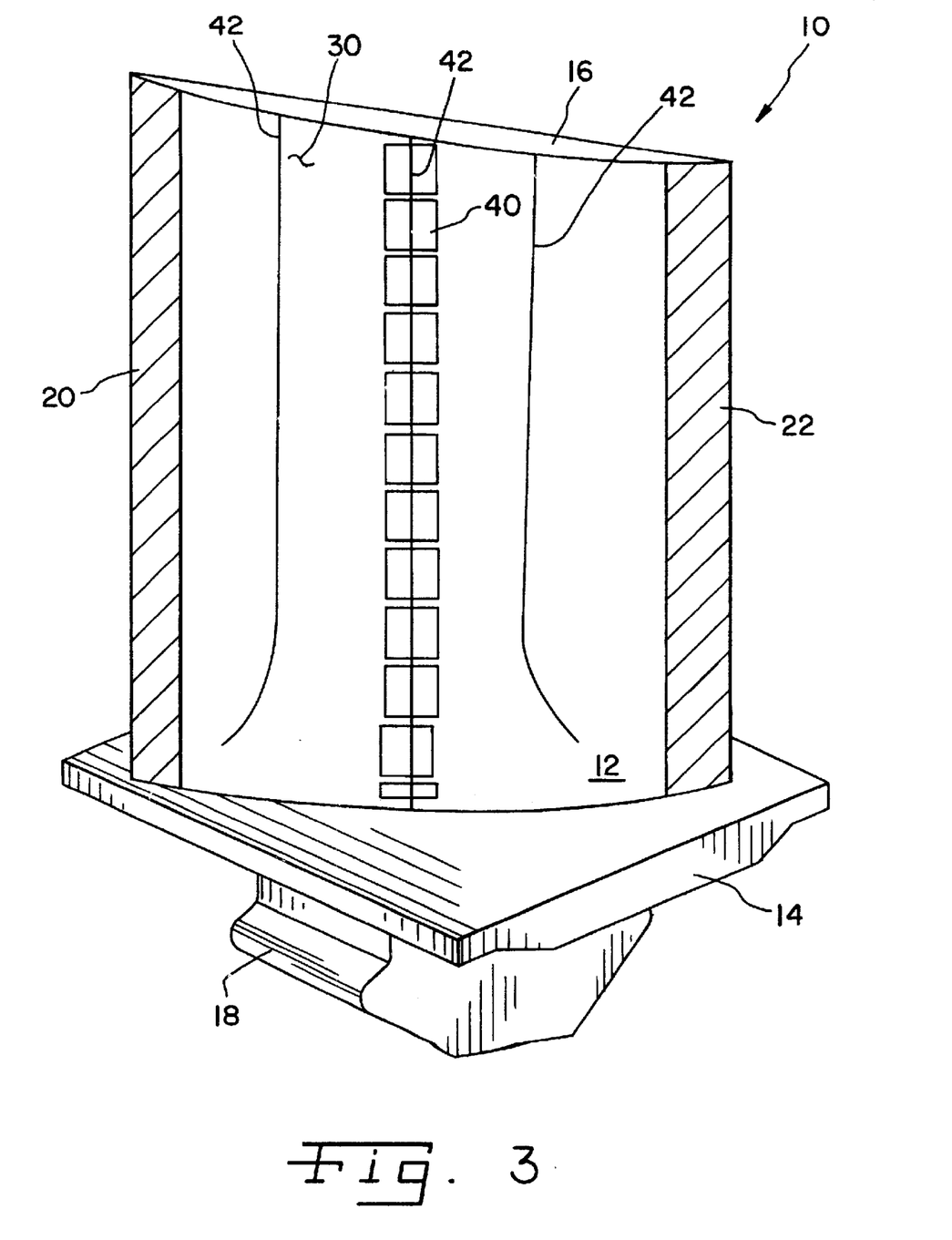
FIG. 3 is a perspective view of a workpiece, such as an aircraft gas turbine engine compressor blade of the present invention.

FIG. 3, shows the workpiece of the present invention, such as a gas turbine engine blade which includes an airfoil 12 extending radially outward from a blade platform 14 to a blade tip 16. Blade 10 includes a root section 18 extending radially inward from the platform to a radially inward end. Airfoil 12 extends in a chordwise direction between a leading edge 20 and a trailing edge 22. Airfoil 12 further includes center surface 30, which separates leading edge 20 and trailing edge 22.

A plurality of laser shock peened regions 40 are shown aligned between nodal lines 42, in this case a 1st-2nd stripe (FIG. 1) torsion mode where there may be maximum bending curvature. Alternatively, laser shock peened regions 40 may be applied to other locations either on or adjacent the different nodal lines of the blade, i.e., such nodal lines shown in FIG. 1 and others known in the art of airfoil design. It should be realized, that different workpieces, and particularly different styles of aircraft gas turbine blades may have different types of nodal characteristics, based upon their geometry and construction materials. Additionally, for improved changes or shifting of the vibratory conditions of resonance of a particular workpiece, it may be necessary to shock at different regions of the same blade, such locations to be determined through experimentation or models, when a problem arises with a particular workpiece during operation.

Figure 4:
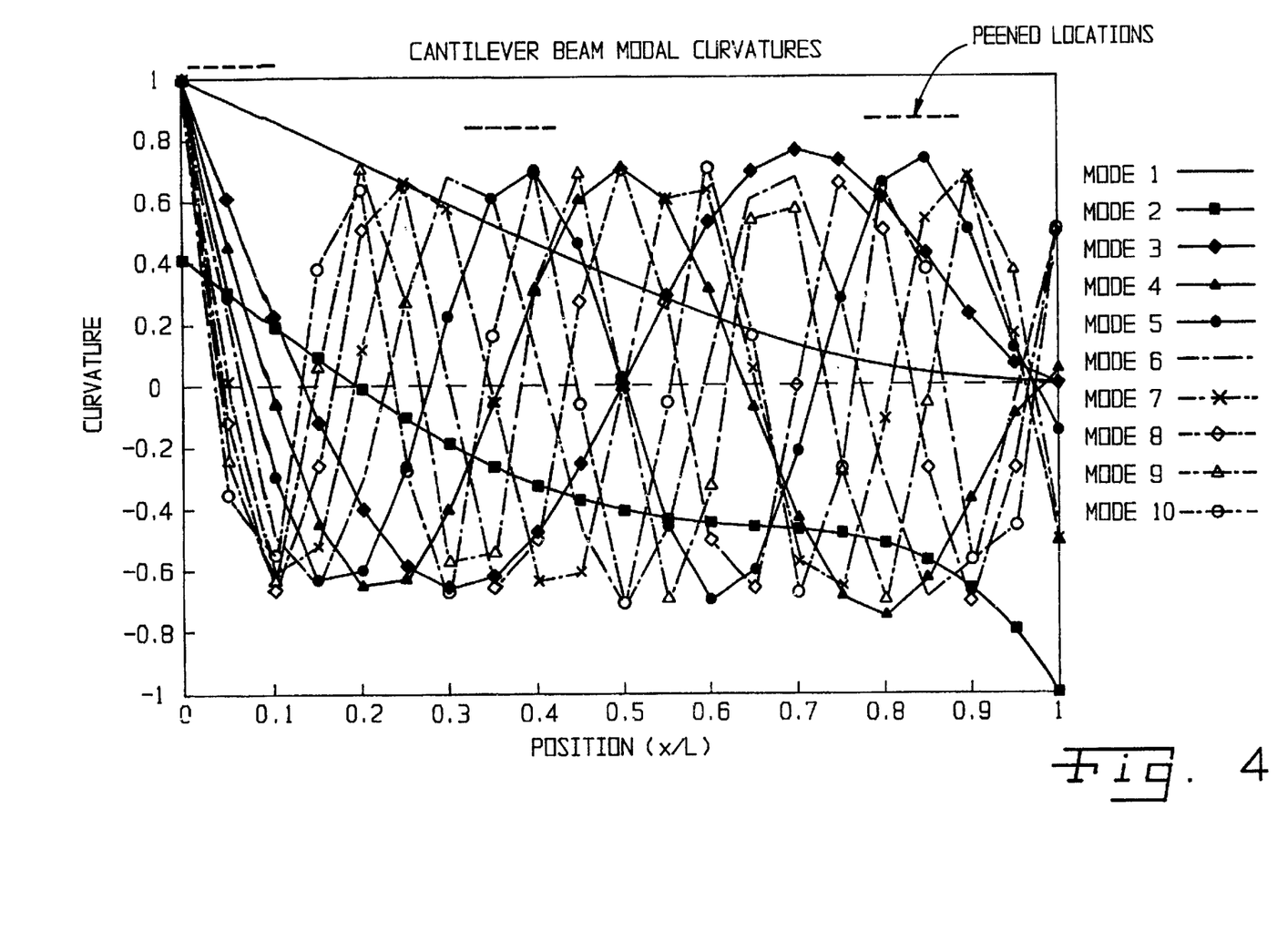
FIG. 4 is a graph of an antilever beam test workpiece vibratory response showing the plurality of vibratory modes.

An example of modifying the vibration damping characteristics, and moving the vibratory resonance condition frequency of a workpiece, has been conducted for test pieces of titanium, steel, and aluminum. Prior to operation of the inventional method, these test pieces, cantilever beams, were analyzed by vibrational analysis procedures. A curvature graph versus distance along the beam was developed for some mode numbers, as shown in FIG. 4, in which the curvature of particular locations, as compared to their modes and were determined.

Application of laser shock peened regions at positions between 0 and 10 percent of the length, and 35 to 45 percent (Distance from root to end of length) was conducted for the first laser peening. These areas were expanded between 0 and 20 percent, and 30 to 50 percent of the beam length for the second laser peening. Each spot was worked on opposite sides of the workpiece via split beam processing. Each spot location was peened three times in both the first and second round of peening.

Figure 5:
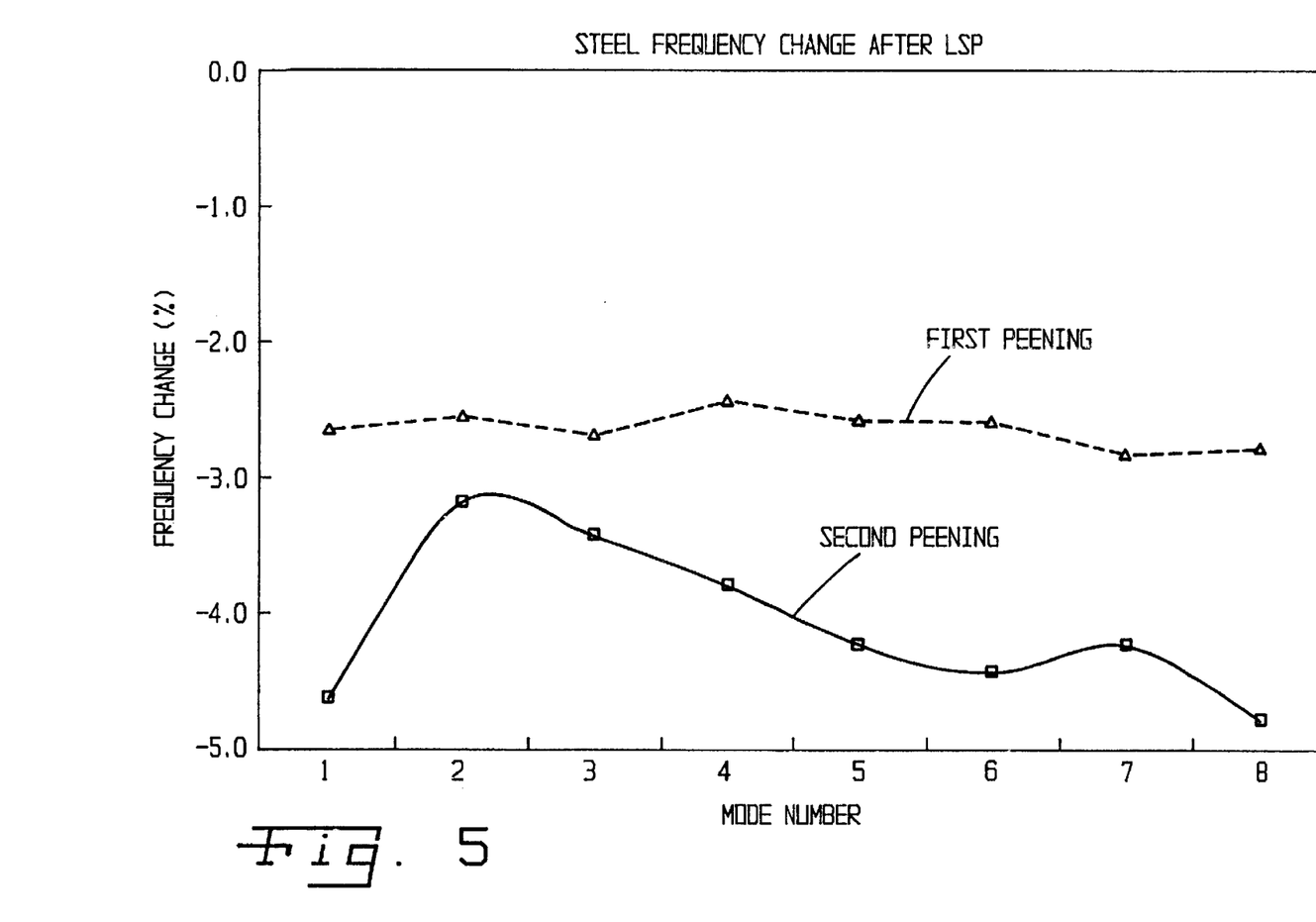
FIG. 5 is a graph of test results of the method of the present invention applied to a steel test piece.
Figure 6:
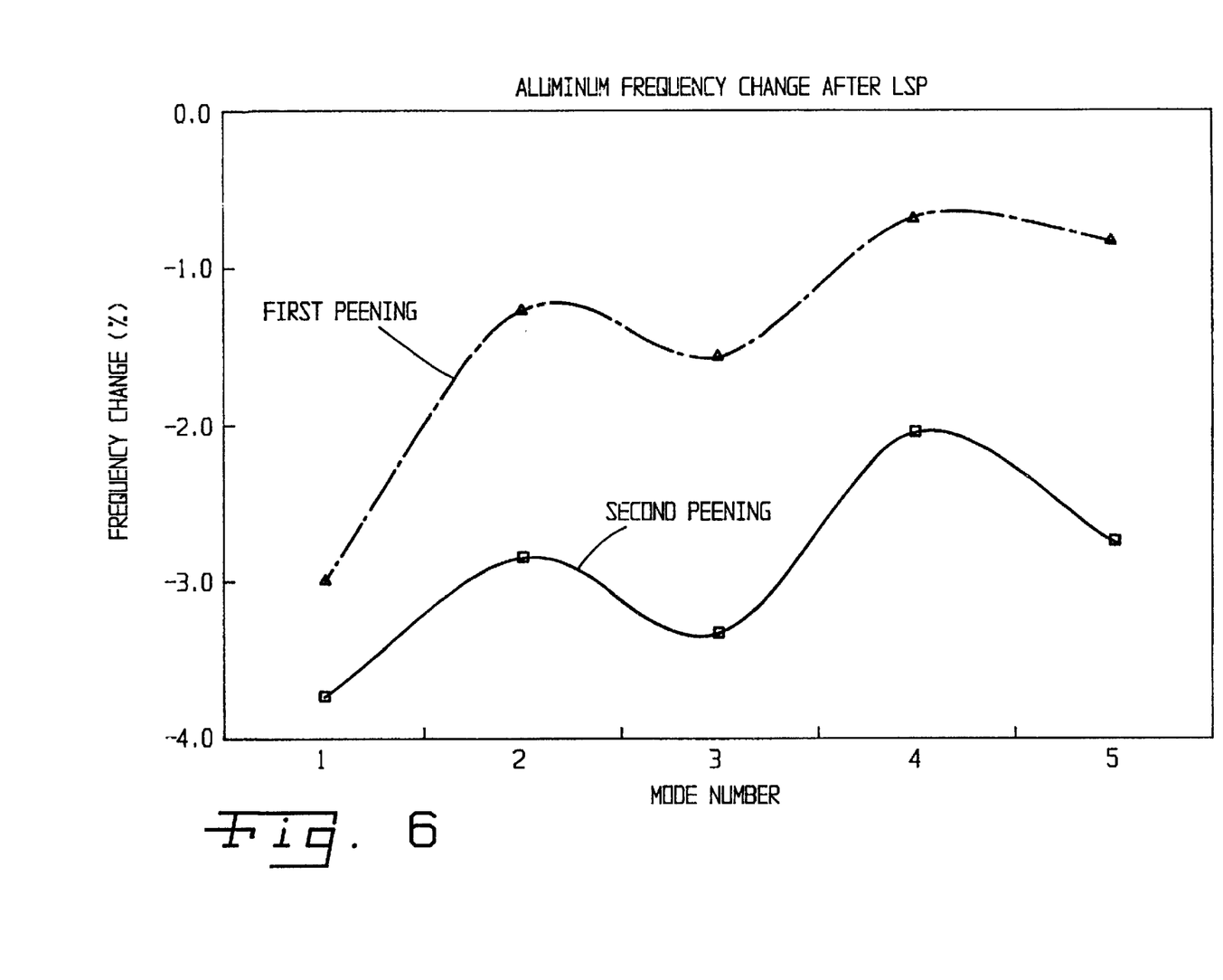
FIG. 6 is a graph of test results of the method of the present invention applied to an aluminum test piece.
Figure 7:
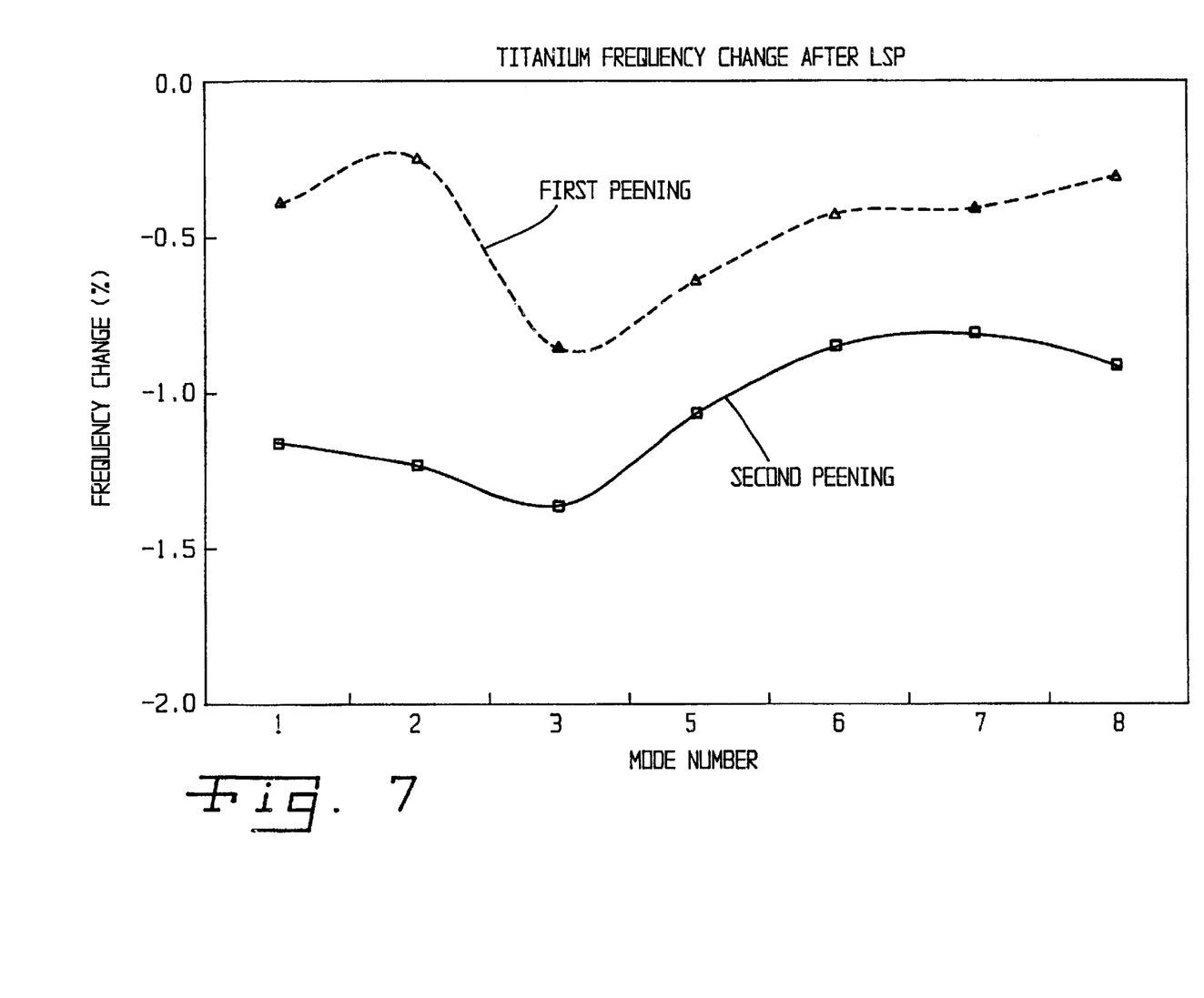
FIG. 7 is a graph of test results of the method of the present invention applied to a titanium test piece.

FIGS. 5, 6, and 7 show the altered vibrational frequency change as compared to the mode number in the first round of laser shock peening. After the first round of peening, data on the frequency response change on each of the different test pieces as compared to particular mode numbers was collected via vibration analysis.

After analysis, the same areas on the three test pieces were laser peened once more (i.e., the second round of peening), and a second graph of frequency response changes compared to mode numbers for each of the particular test pieces was created.

Each of the materials laser peened showed changes in frequency after each laser shock peening. The incremental changes were in the same direction and nominally the same for each treatment. This indicates that there changes were not simple scatter, but were actual, progressive, frequency changes caused by the residual compressive stresses introduced by laser peening.

As shown for the titanium test piece, laser shock processing changed the frequency response condition frequency approximately 0.5 percent after each laser peening for a total of one percent frequency change. The aluminum test piece as shown in FIG. 6, changed approximately 1 percent after the first laser peening and about 2 percent after the second, for a total change of three percent in its vibratory frequency response. The best vibratory resonance condition frequency change was shown in the steel test piece having an approximately 2.8 percent change after the first laser peening followed by a 0.5 to 2 percent change after the second shocking, for a total of about four percent frequency change. Such frequency changes would be sufficient to enhance the operating envelope of workpieces, such as gas turbine engine airfoils, partially by laser shock peening larger areas and at higher intensities.

Figure 8:
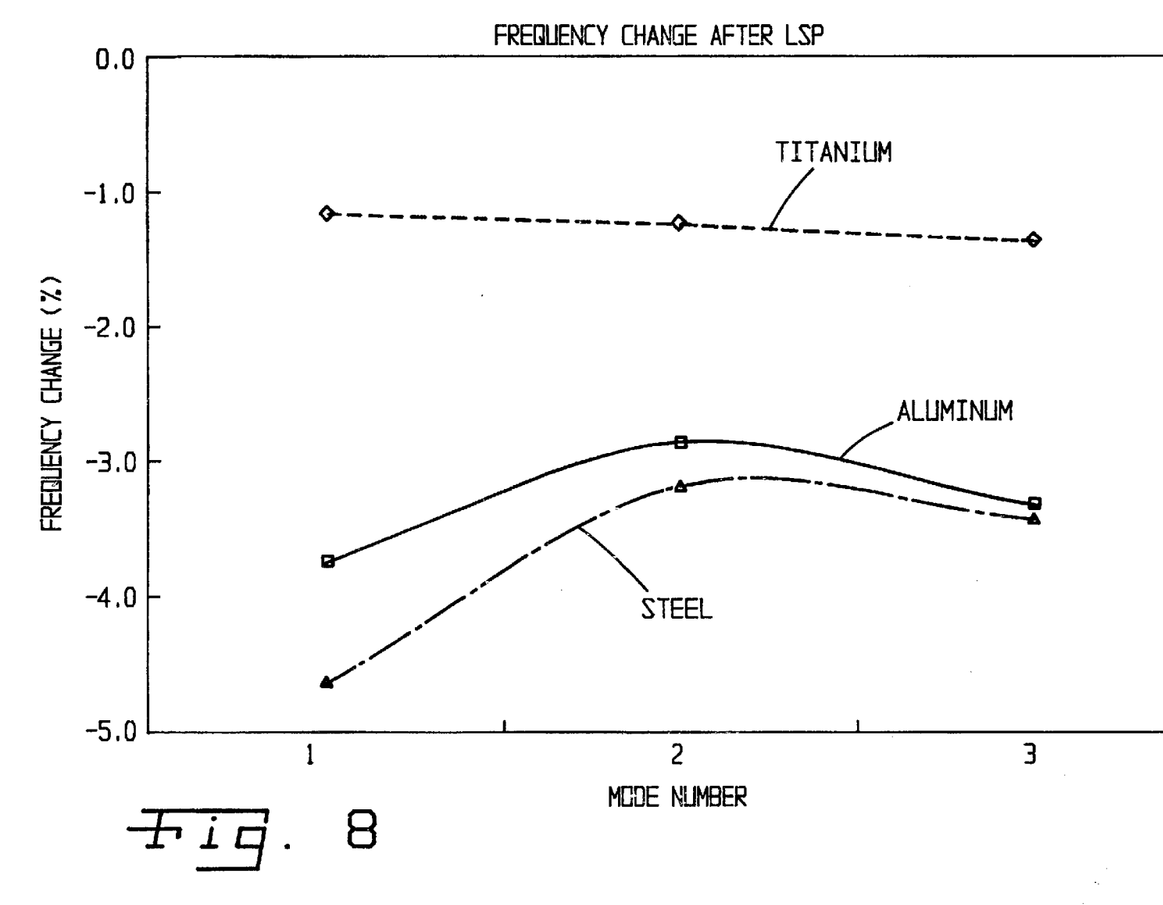
FIG. 8 is a graph showing the above three test pieces' frequency change for the first three modes after laser shock peening.

FIG. 8 shows the comparison to frequency change between the titanium, aluminum, and steel test coupons for the first three modes only.

Experimental evidence for different-shaped workpieces needs to be determined for a particular area to be laser shock peened to counteract particular modes and vibration resonance condition frequencies. Models, particularly finite element modeling, can be developed and used to determine the appropriate areas and intensities of laser peening when the depths and magnitudes of the residual compressive stresses are known. With the present invention it is taught that residual compressive stressors do change the vibration frequencies of workpieces. Models can be developed to practice changes in the vibratory resonance condition of a particular mode. Particular areas to be laser shock peened on a particular part may be determined via experimentation, observation, and or modeling of these responses.

Figure 9:
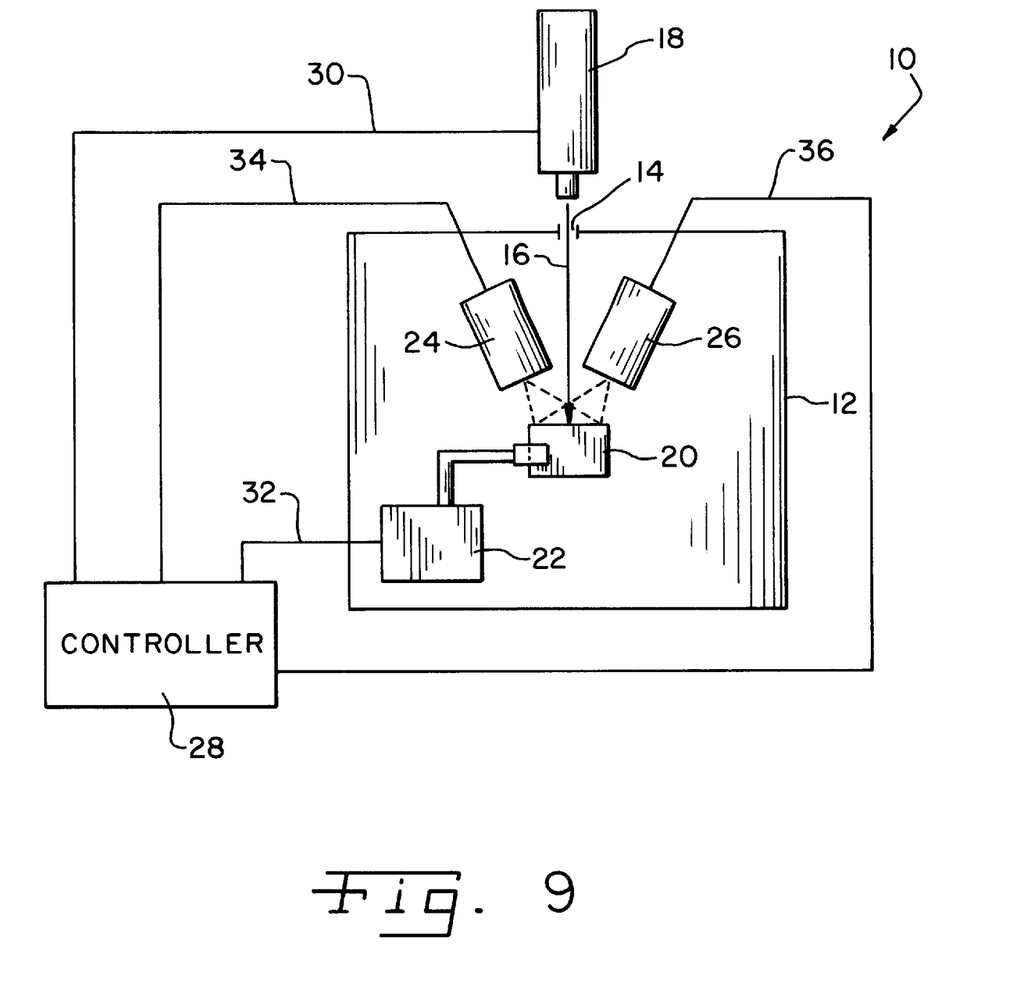
FIG. 9 is a drawing of one form of the laser peening apparatus showing an operatively associated natural frequency measurement device.

FIG. 9 shows an embodiment of the present invention with a typical laser shock processing apparatus 10 comprises a target chamber 12 with an opening 14 for a laser beam 16 created by laser 18, a source of coherent energy. Laser 18, by way of example, may be a commercially available high power pulse laser system capable of delivering more than approximately 40 joules in 5 to 100 nanoseconds. The laser pulse length and focus of the laser beam may be adjusted as known in the art. As shown in FIG. 1, a workpiece 20 is held in position within target chamber 12 by means of a positioning mechanism 22. The vibration response means, or natural frequency determination measurement device may be incorporated directly into positioning mechanism 22 or may be a physically separate measurement device. Various mechanism and means for determining the natural frequency of a workpiece are know.

Apparatus 10 includes a material applicator 24 for applying an energy absorbing material onto workpiece 20 to create a "coated" portion. Material applicator 24 may be that of a solenoid-operated painting station or other construction such as a jet spray or aerosol unit to provide a small coated area on workpiece 20. Apparatus 10 further includes a transparent overlay application 26 that applies a fluid or liquid transparent overlay to workpiece 10 over the portion coated by material applicator 24. Transparent overlay material should be substantially transparent to the radiation, water being the preferred overlay material.

A controller, depicted as block 28, may be utilized to store and compare the natural frequency response and data of the present invention. A preferred example of a controller would be an appropriated programmed personal or microcomputer or PLC. Such a computer or controller 28 operates to accomplish the control of the laser system and comparing functions of the method, to enable real time natural frequency measurements and utilization in real time.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for determining that a production workpiece has been sufficiently laser shock peened, the method comprising the steps of:
    determining a natural frequency of a test workpiece before laser shock peening said test workpiece;
    determining the frequency shift of said natural frequency of said test workpiece after said test workpiece has been laser shock peened;
    comparing said frequency shift to a predetermined acceptable range of frequency shift for said test workpiece;
    processing production workpieces if said frequency shift is within said acceptable range of frequency shift.

2. The method of claim 1 wherein said test workpiece is also a production workpiece.

3. The method of claim 1 in which said acceptable range of frequency shift is determined through fatigue testing of laser shock peened production workpieces.

4. The method of claim 1 in which said acceptable range of frequency shift is determined through destructive testing of production workpieces.

5. The method of claim 1 in which said predetermined natural frequency shift is determined by computational means.

6. The method of claim 1 in which said natural frequency is a mode that exhibits the largest response to laser shock peening for the test workpiece.

7. The method of claim 1 further comprising the step of laser shock peening said laser shock peened test workpiece.

8. The method of claim 1 in which said workpiece is a gas turbine engine blade.

9. A method for determining that the laser shock peening processing conditions are within an acceptable range, the method comprising the steps of:
    determining a natural frequency of a test workpiece before laser shock peening said test workpiece;
    determining the frequency shift of said natural frequency of said test workpiece after said test workpiece has been laser shock peened;
    comparing said frequency shift to a predetermined acceptable range of frequency shift for said test workpiece;
    processing production workpieces if said frequency shift is within said acceptable range of frequency shift.

10. The method of claim 9 wherein said test workpiece is also a production workpiece.

11. The method of claim 9 in which said acceptable range of frequency shift is determined through fatigue testing of the production workpieces.

12. The method of claim 9 in which said acceptable range of frequency shift is determined through destructive testing of the production workpieces.

13. The method of claim 9 in which said predetermined natural frequency is determined by computational means.

14. The method of claim 9 in which said natural frequency is a mode that exhibits the largest response to laser shock peening for the test workpiece.

15. The method of claim 9 further comprising the step of laser shock peening said laser shock peened test workpiece.

16. The method of claim 9 in which said workpiece is a gas turbine engine blade.

17. A method for determining that a workpiece has been sufficiently laser shock processed, the method comprising the steps of:

determining a natural frequency of a laser peened workpiece;

comparing said determined natural frequency to a predetermined natural frequency indicative of a sufficiently lasers shock peened workpiece.

18. The method of claim 17 in which said predetermined natural frequency is determined by empirically measuring a vibration response on a test workpiece.

19. The method of claim 17 in which said predetermined natural frequency is determined by computational means.

20. The method of claim 17 further comprising the step of laser peening said laser peened workpiece.

* * * * *